United States Patent
Ishida

(10) Patent No.: US 10,279,149 B2
(45) Date of Patent: *May 7, 2019

(54) CATHETER ASSEMBLY WITH GUIDEWIRE, CATHETER AND PUNCTURE NEEDLE

(71) Applicant: Terumo Kabushiki Kaisha, Shibuya-ku, Tokyo (JP)

(72) Inventor: Masahiro Ishida, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/014,259

(22) Filed: Jun. 21, 2018

(65) Prior Publication Data

US 2018/0304047 A1 Oct. 25, 2018

Related U.S. Application Data

(63) Continuation of application No. 15/941,632, filed on Mar. 30, 2018, which is a continuation of application (Continued)

(30) Foreign Application Priority Data

Jun. 12, 2013 (JP) ................................. 2013-123465

(51) Int. Cl.
*A61M 25/06* (2006.01)
*A61M 25/09* (2006.01)
(Continued)

(52) U.S. Cl.
CPC ........ *A61M 25/0606* (2013.01); *A61M 5/158* (2013.01); *A61M 25/0097* (2013.01);
(Continued)

(58) Field of Classification Search
CPC ........ A61M 25/0606; A61M 25/09041; A61M 25/0169; A61M 25/09; A61M 2025/0177
See application file for complete search history.

(56) References Cited

U.S. PATENT DOCUMENTS 4,525,157 A 6/1985 Vaillancourt
4,652,256 A 3/1987 Vaillancourt
(Continued)

FOREIGN PATENT DOCUMENTS

CN 101242868 A 8/2008
CN 102939129 A 2/2013
(Continued)

OTHER PUBLICATIONS

International Search Report (PCT/ISA/210) dated Apr. 28, 2014, by the Japanese Patent Office as the International Searching Authority for International Application No. PCT/JP2014/058490.
(Continued)

*Primary Examiner* — Kevin C Sirmons
*Assistant Examiner* — Leah J Swanson
(74) *Attorney, Agent, or Firm* — Buchanan Ingersoll & Rooney PC

(57) ABSTRACT

A catheter assembly includes a catheter, a catheter hub fixed to the proximal end of the catheter, a needle positioned inside the catheter, a gripping member connected to a proximal portion of the inner needle, a catheter operating member connected to the catheter hub and movable in the longitudinal direction relative to the inner needle, a guide wire slidably positioned in the inner needle and possessing a length longer than both the inner needle and the catheter, and a wire operating member connected to the guide wire so that movement of the wire operating member results in movement of the guide wire. The catheter operating member is configured to press a portion of the catheter between the
(Continued)

proximal end of the catheter and the distal end of the catheter when the user presses on the catheter operating member while puncturing a living body with the needlepoint.

20 Claims, 18 Drawing Sheets

Related U.S. Application Data

No. 15/083,965, filed on Mar. 29, 2016, now Pat. No. 10,004,878, which is a continuation of application No. 14/960,484, filed on Dec. 7, 2015, now Pat. No. 10,099,038, which is a continuation of application No. PCT/JP2014/058490, filed on Mar. 26, 2014.

(51) Int. Cl.
  *A61M 5/158* (2006.01)
  *A61M 25/00* (2006.01)
  *A61M 25/01* (2006.01)

(52) U.S. Cl.
  CPC .... *A61M 25/0108* (2013.01); *A61M 25/0612* (2013.01); *A61M 25/0631* (2013.01); *A61M 25/09041* (2013.01)

(56) References Cited

U.S. PATENT DOCUMENTS

| | | | |
|---|---|---|---|
| 5,366,441 A | 11/1994 | Crawford | |
| 6,197,001 B1 | 3/2001 | Wilson | |
| 6,953,448 B2 | 11/2005 | Moulton | |
| 2010/0094310 A1 | 4/2010 | Warring et al. | |
| 2011/0282285 A1 | 11/2011 | Blanchard | |
| 2013/0023826 A1 | 1/2013 | Ishida | |

FOREIGN PATENT DOCUMENTS

| | | |
|---|---|---|
| EP | 1 378 263 A2 | 1/2004 |
| JP | 2012-5647 A | 1/2012 |
| JP | 2012-205692 A | 10/2012 |
| JP | 5108882 B2 | 12/2012 |
| WO | WO2011/118643 A1 | 9/2011 |
| WO | WO2011/143621 A1 | 11/2011 |

OTHER PUBLICATIONS

European Search Report dated Feb. 6, 2017, by the European Patent Office in corresponding European Application No. 14811087.7 (7 pgs).

Notification of Refusals dated Dec. 28, 2016, by the Japanese Patent Office in corresponding Japanese Patent Application No. 2016-059718 (4 pgs).

Extended European Search Report dated Jul. 18, 2017, by the European Patent Office in corresponding European Application No. 14811087.7 (14 pgs).

Official Action dated Jul. 24, 2017 by the Chinese Patent Office in counterpart Chinese Patent Application No. 201480018070.8 (10 pgs).

Official Action dated Aug. 31, 2017 by the Japanese Patent Office in counterpart Japanese Patent Application No. 2015-522600 (6 pgs).

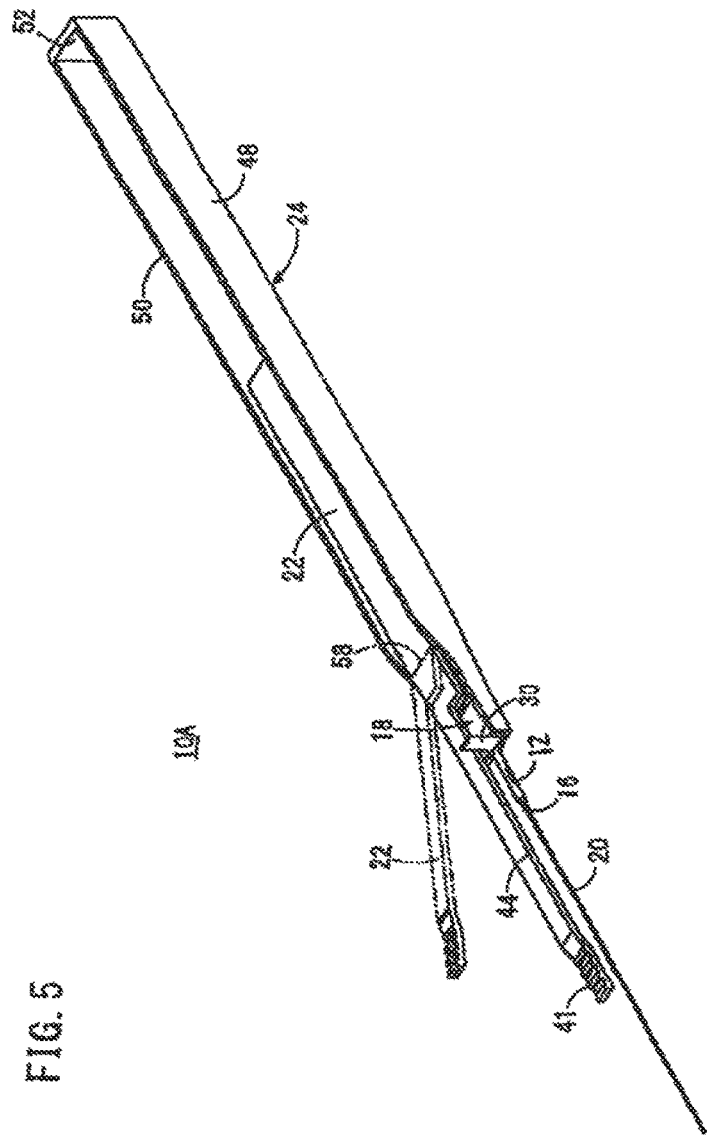

ion of U.S. application Ser. No. 14/960,484 filed on Dec. 7, 2015, which is a continuation of International Application No. PCT/JP2014/058490 filed on Mar. 26, 2014, and claims priority to Japanese Application No. 2013-123465 filed on Jun. 12, 2013, the entire content of all of which is incorporated herein by reference.

CATHETER ASSEMBLY WITH GUIDEWIRE, CATHETER AND PUNCTURE NEEDLE

CROSS-REFERENCES TO RELATED APPLICATIONS

This application is a continuation of U.S. application Ser. No. 15/941,632 filed on Mar. 30, 2018, which is a continuation of U.S. application Ser. No. 15/083,965 filed on Mar. 29, 2016, which is a continuation of U.S. application Ser. No. 14/960,484 filed on Dec. 7, 2015, which is a continuation of International Application No. PCT/JP2014/058490 filed on Mar. 26, 2014, and claims priority to Japanese Application No. 2013-123465 filed on Jun. 12, 2013, the entire content of all of which is incorporated herein by reference.

TECHNICAL FIELD

The present invention generally relates to a catheter assembly adapted to puncture a blood vessel and indwelled at the time of performing infusion to a patient, for example.

BACKGROUND DISCUSSION

A catheter assembly is used at the time of performing infusion to a patient or the like. This kind of catheter assembly includes a hollow outer needle (catheter), an outer needle hub (catheter hub) fixed to a proximal end of the outer needle, an inner needle inserted into the outer needle and having a sharp needlepoint at a distal end, and an inner needle hub fixed to a proximal end of the inner needle. In the case of performing infusion to the patient by using the catheter assembly, a blood vessel of the patient is punctured with the outer needle together with the inner needle. After puncturing, the inner needle is pulled out from the outer needle while keeping the patient punctured with the outer needle. Next, a connector provided at an end portion of an infusion tube is connected to a proximal end of the outer needle hub, and infusion material is supplied into the blood vessel of the patient via the infusion tube, outer needle hub, and outer needle. An example of such a catheter assembly used as a peripheral intravenous catheter is disclosed in Japanese Patent No. 5108882.

A central intravenous catheter, a peripherally inserted central catheter (PICC), a midline catheter, etc. are known as catheters having a length longer than the peripheral intravenous catheter, indwelled inside a blood vessel of a patient, and used to administer infusion solution. Therefore, when respective lengths of the inner needle and the catheter of the catheter assembly are long, it is possible to use as the central intravenous catheter, PICC, midline catheter, etc.

SUMMARY

However, when the lengths of an inner needle and a catheter are relatively long, puncturing is difficult because the inner needle and the catheter may be deflected at the time of a puncturing operation. Further, when there are meandering and branching in a blood vessel, insertion is difficult at the time of inserting the catheter up to a predetermined position inside the blood vessel.

A catheter assembly is disclosed here to relatively easily perform the puncturing operation even in the case where the lengths of the inner needle and the catheter are relatively long, and further configured to rather easily insert the catheter into the blood vessel.

According to one aspect, a catheter assembly comprises: a catheter possessing a distal end, a proximal end and a proximal end portion; a catheter hub fixed to the proximal end portion of the catheter, and possessing a proximal-most end; a hollow inner needle positioned inside the catheter and removable from inside the catheter, with the needle possessing a distal end and including a needlepoint at the distal end of the needle; a gripping member connected to a proximal portion of the inner needle and extending in a longitudinal direction; and a catheter operating member connected to the catheter hub and movable in the longitudinal direction relative to the inner needle, wherein the catheter operating member includes an operating portion. The operating portion of the catheter operating member possesses a part to which a force is applied by a user to move the catheter relative to the inner needle from a position in which a distal-most end of the catheter is positioned proximal to the needlepoint to a position in which the distal-most end of the catheter is positioned distal to the needlepoint. A guide wire is slidably positioned in the inner needle and possesses a distal end, with the guide wire possessing a length longer than the inner needle and longer than the catheter, and with the guide wire being configured so that the distal end of the guide wire projects distally beyond the needlepoint during use of the catheter assembly. A wire operating member is connected to the guide wire so that movement of the wire operating member results in movement of the guide wire. The wire operating member is movable in the longitudinal direction relative to the inner needle and the catheter, and the wire operating member includes an operating portion. The wire operating member that moves together with the guide wire possesses a distal-most end that axially overlaps a part of the catheter operating member when the distal-most end of the catheter is positioned proximal of the needlepoint before use of the catheter assembly. The operating portion of the wire operating member possesses a part to which a force is applied by the user to move the guide wire relative to the catheter and the inner needle. The catheter operating member is configured to press a portion of the catheter between the proximal end of the catheter and the distal end of the catheter when the user presses on the catheter operating member while puncturing a living body with the needlepoint.

BRIEF DESCRIPTION OF THE DRAWINGS

FIG. 5 is a first view illustrating a using method of the catheter assembly illustrated in FIG. 1.

DETAILED DESCRIPTION

Set forth below, with reference to the accompanying drawing figures, is a detailed description of embodiments of a catheter assembly representing examples of the inventive catheter assembly disclosed here.

Figure 1:
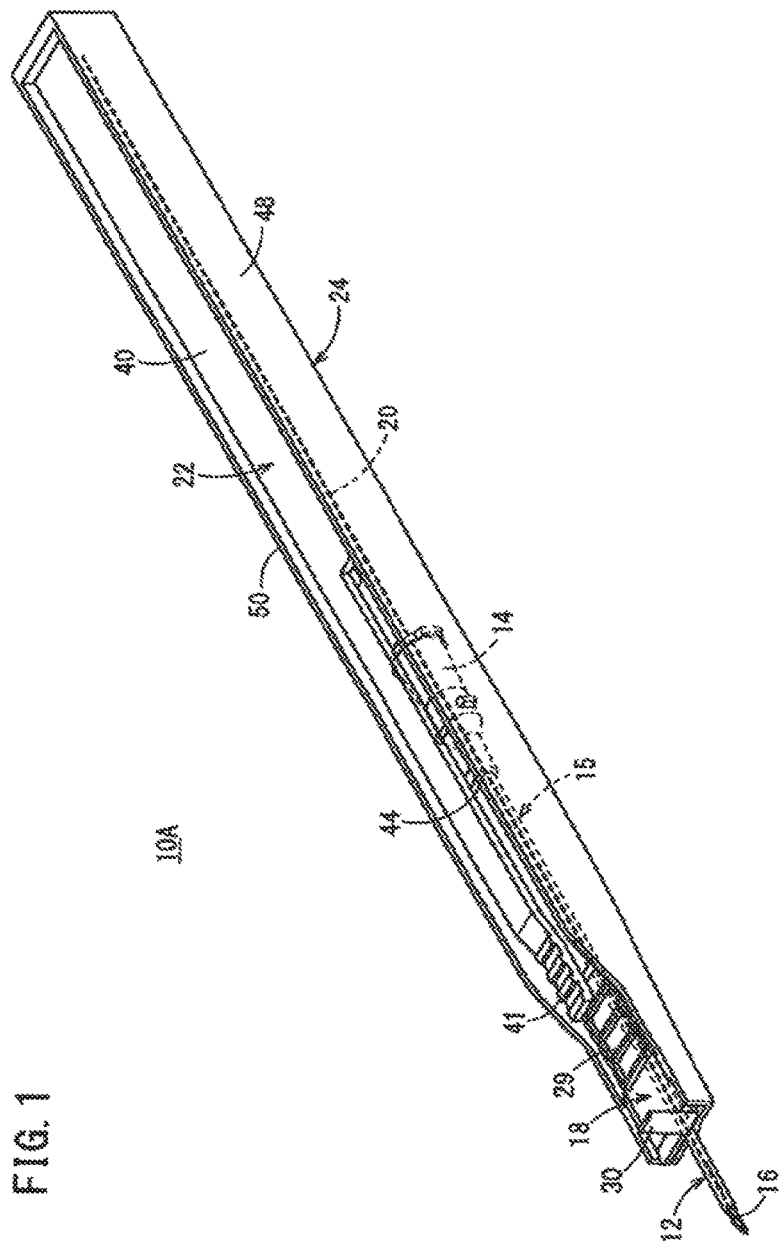
FIG. 1 is a perspective view illustrating a catheter assembly according to a first embodiment disclosed here.
Figure 2:
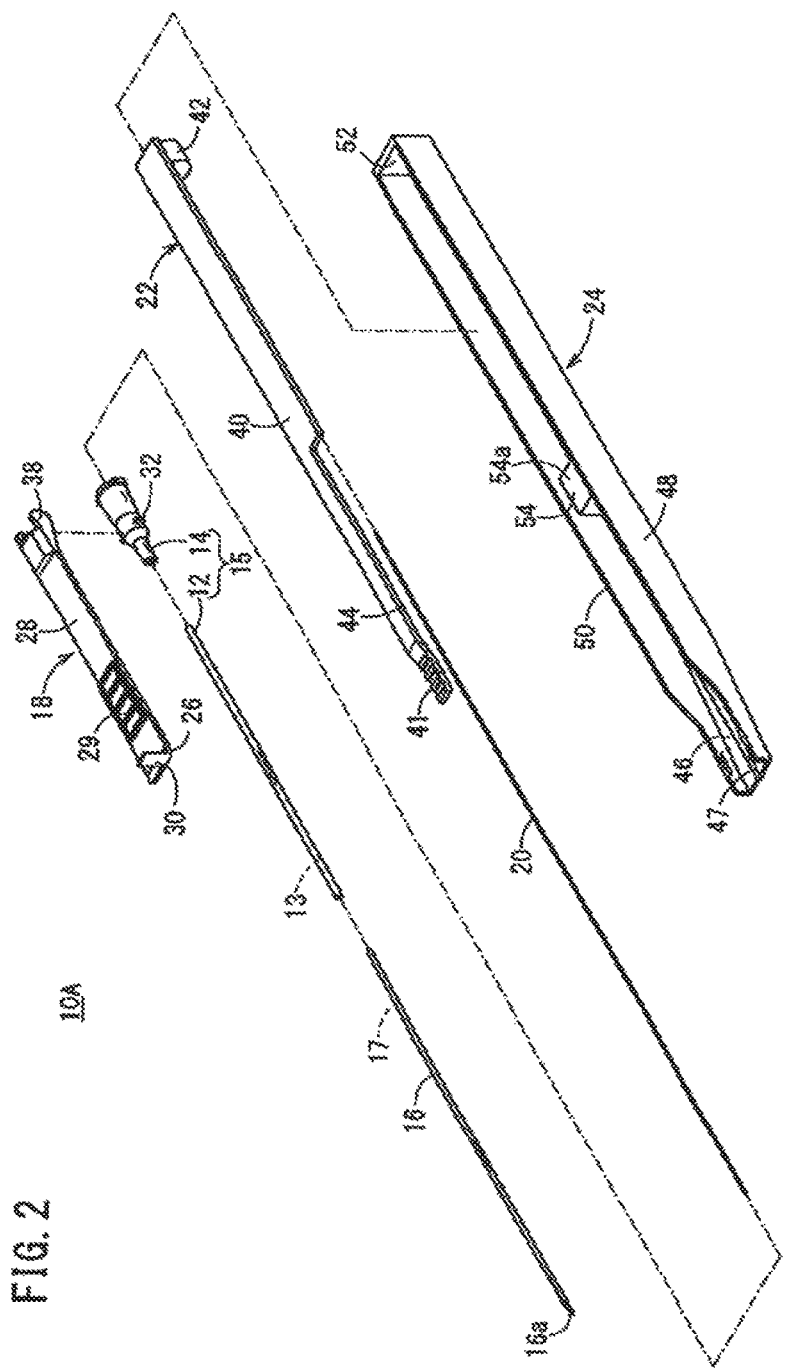
FIG. 2 is an exploded perspective view illustrating the catheter assembly illustrated in FIG. 1.
Figure 3:
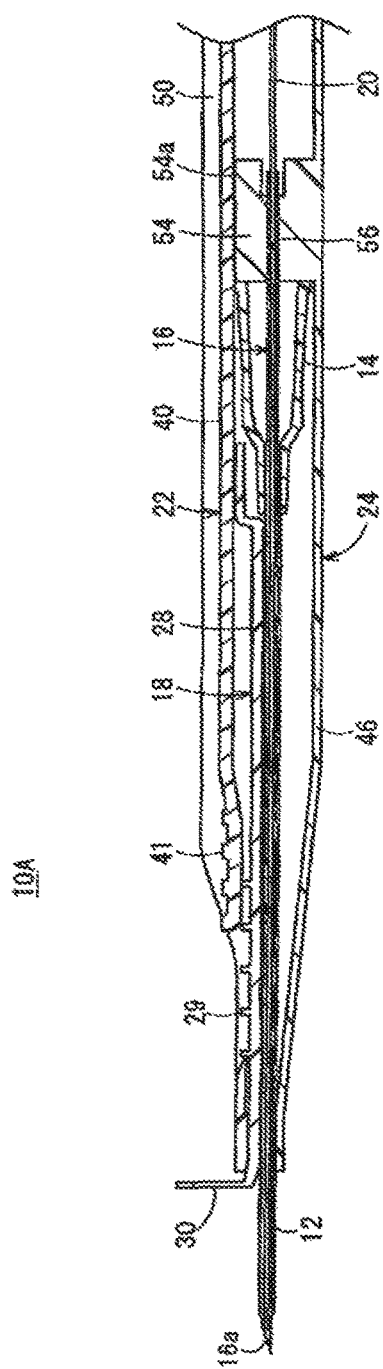
FIG. 3 is a partly-omitted vertical cross-sectional view illustrating the catheter assembly illustrated in FIG. 1.

FIGS. 1-3 illustrate an example of the inventive a catheter assembly 10A disclosed here according to a first embodiment.

The catheter assembly 10A is gripped and operated by a user (doctor, nurse, etc.) in an initial state illustrated in FIG. 1, and a blood vessel of a patient is punctured with a distal end of the catheter assembly 10A. Then, predetermined respective operations are performed, and only a catheter member 15 adapted to puncture the blood vessel and inserted into the blood vessel is indwelled on the patient's side. Further, a connector of an infusion tube (not illustrated) is connected to a proximal end portion of the catheter member 15, thereby supplying infusion material (chemical solution) to the patient from the infusion tube. Set forth next is a detailed description of the structure of the catheter assembly 10A.

The catheter assembly 10A includes a catheter 12, a catheter hub 14 connected to the catheter 12, an inner needle 16 inserted into or positioned inside the catheter 12, a pressing member 18 connected to the catheter hub 14, a guide wire 20 inserted into or positioned inside the inner needle 16, a wire operating member 22 connected to the guide wire 20, and a gripping member 24 connected to the inner needle 16.

The catheter 12 functions as an outer needle, and is a flexible tubular member formed to have a predetermined length and a relatively small diameter. The catheter assembly 10A has a double tube structure in which the inner needle 16 is inserted into or positioned inside the catheter 12 in the initial state before use (before puncturing the patient), and the inner needle 16 projects distally beyond a distal end of the catheter 12 by a predetermined length. In the following description, the initial state of the catheter assembly 10A may also be referred to as an "assembled state". Inside the catheter 12, a lumen 13 extending in an axial direction is formed and penetrates the inside of the catheter 12. The inner diameter of the lumen 13 is set to a size permitting the inner needle 16 to be inserted into the lumen 13 of the catheter 12.

A constituent material of the catheter 12 (i.e., the material from which the catheter 12 is made) is resin material, and particularly a flexible resin material is preferable. In this case, specific examples may include fluororesins such as polytetrafluoroethylene (PTFE), ethylene-tetrafluoroethylene copolymer (ETFE), perfluoroalkoxy fluororesin (PFA), olefin resins such as polyethylene and polypropylene, or mixtures thereof, polyurethane, polyesters, polyamides, polyether nylon resins, and mixtures of the olefin resin and ethylene-vinyl acetate copolymer, and the like.

The catheter 12 may be formed of a clear resin such that the entirety of the inside of the catheter 12, or a part of the inside of the catheter 12, can be visually checked or observed. The catheter 12 may include radiopaque (opaque to X-ray) material (such as barium monoxide) to have an imaging function.

A length of the catheter 12 is not particularly limited and suitably is set in accordance with a purpose of use, other conditions, and so on. For example, the length of the catheter 12 is about 20 to 500 mm, preferably about 30 to 400 mm, and more preferably about 100 to 300 mm.

The catheter 12 may be used as, for example, a catheter having the length longer than a peripheral intravenous catheter such as a central intravenous catheter, a PICC, or a midline catheter. The catheter 12 may also be used as the peripheral intravenous catheter.

As illustrated in FIG. 3, the catheter hub 14 is liquid-tightly connected and fixed to the proximal end of the catheter 12. Specific examples of a means to fix the catheter hub 14 to the catheter 12 include crimping, fusion (heat-fusion, high-frequency fusion, etc.), adhesion by an adhesive, etc. The catheter hub 14 is configured as a tube having a taper shape. The catheter member 15 is formed by joining the catheter 12 with the catheter hub 14.

The constituent material forming the catheter hub 14 is not particularly limited, but various kinds of resin materials may be used, for example, polyolefins such as polyethylene, polypropylene, and ethylene-vinyl acetate copolymer, polyurethane, polyamides, polyester, polycarbonate, polybutadiene, polyvinyl chloride, polyacetal, and so on.

At the time of using the catheter assembly 10A, the catheter hub 14 is exposed or positioned on the skin of the patient in a state that the blood vessel is punctured with the catheter 12, and the catheter hub 14 is pasted or held on the skin by using tape or the like for indwelling. Preferably, the catheter hub 14 is formed of material harder than the catheter 12. The constituent material for fabricating the catheter hub 14 is not particularly limited, but specific examples may preferably include thermoplastic resins such as polypropylene, polycarbonate, polyamides, polyether sulfone, polyarylate, and methacrylate-butyrene-styrene copolymer.

The inner needle 16 is a hollow member including a distal end opening, a proximal end opening, and a lumen 17 extending between the distal end opening and the proximal end opening. Further, the inner needle 16 includes a sharp needlepoint 16a at a distal end of the inner needle 16. The inner needle 16 has a length longer than the catheter 12. When the catheter assembly 10A is in the assembled state, the needlepoint 16a projects distally beyond the distal end opening of the catheter 12, and a proximal end of the inner needle 16 projects proximally beyond the proximal end portion of the catheter member 15 (catheter hub 14). Further, in the assembled state, a middle portion in the longitudinal direction of the inner needle 16 is inserted into or positioned inside the catheter hub 14.

The inner needle 16 has rigidity allowing the inner needle 16 to puncture the skin of the patient. Specific examples of a constituent material for fabricating the inner needle 16 may include metallic materials such as stainless steel, aluminum or an aluminum alloy, or titanium or a titanium alloy.

The pressing member 18 is connected to the catheter hub 14, and, in the assembled state, is configured to press a portion between the proximal end and the distal end of the catheter 12 (middle portion or intermediate portion in the longitudinal direction of the catheter 12) at the time of performing a puncturing operation to puncture the blood vessel with the needlepoint 16*a* of the inner needle 16 and the distal end portion of the catheter 12. More specifically, the pressing member 18 includes a pressing portion 26 configured to press the portion of the catheter 12 between the proximal end of the catheter 12 and the distal end of the catheter 12. The pressing portion 26 is a component to prevent the inner needle 16 and the catheter 12 from being deflected at the time of the puncturing operation.

Further, the pressing member 18 is disposed in the axial direction (longitudinal direction) of the catheter 12 which is in a linear state, and includes: a long main body 28 positioned above the catheter 12; and a finger hook projection 30 disposed at the main body 28, projecting away from the main body 28 and adapted to hook a finger. The upper surface of the main body 28 possesses an uneven shape 29, and functions as a slip stopper at the time of operating with a finger.

The finger hook projection 30 in the illustrated present example projects upward from the distal end of the main body 28. The finger hook projection 30 may project upward from the proximal end side slightly more than the distal end of the main body 28. That is, the finger hook projection 30 can project upwardly from the main body 28 at a position that is proximal of the distal end of the main body 28 (i.e., the finger hook projection 30 is located between the distal end of the main body 28 and the middle of the main body.) Or, the finger hook projection 30 may project upward from the middle of the main body 28 in the longitudinal direction (between the distal end and the proximal end) of the main body 28. In the present example illustrated, the above-described pressing portion 26 is formed by the bottom portion of the distal end of the main body 28. The pressing portion 26 may also be formed as a projection projecting downward from the distal end portion of the main body 28.

The pressing portion 26 is disposed at a portion where the inner needle 16 and the catheter 12 can be effectively prevented from being deflected at the time of the puncturing operation. For example, a distance from a most distal end position of the catheter 12 to a portion pressed by the pressing portion 26 is about 8 to 60 mm, preferably, about 10 to 30 mm.

Figure 4A:
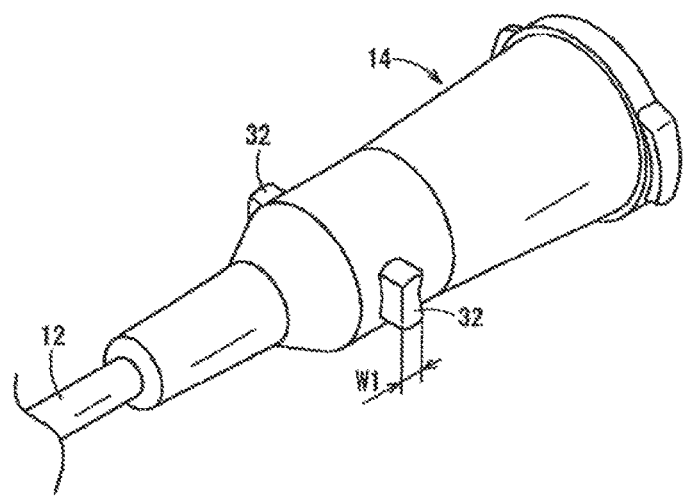
FIG. 4A is a perspective view illustrating a catheter hub in the catheter assembly illustrated in FIG. 1.
Figure 4B:
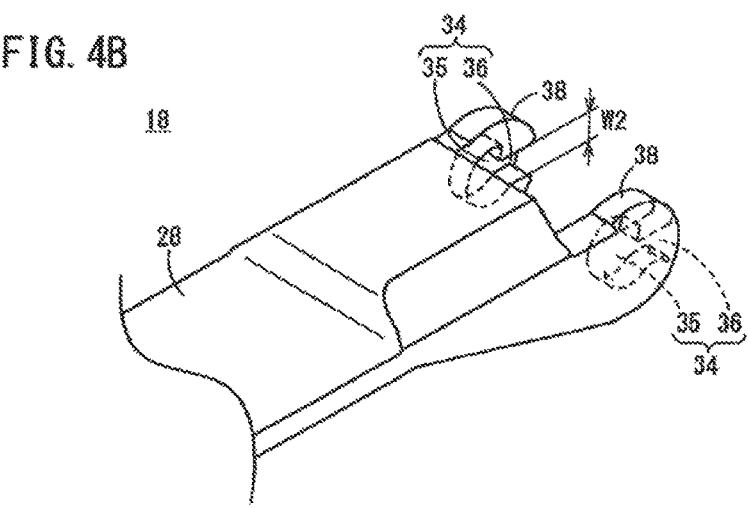
FIG. 4B is a perspective view illustrating a proximal end side of a pressing member in the catheter assembly illustrated in FIG. 1.

The pressing member 18 is connected to the catheter hub 14 in a manner rotatable with respect to the catheter hub 14. As illustrated in FIG. 4A, support projections 32 projecting outward are disposed on outer surfaces on both right and left sides of the catheter hub 14 in the illustrated present example. The respective support projections 32 extend in a vertical direction. As illustrated in FIG. 4B, a pair of connection pieces 38 (right and left connection pieces 38) that each include connection grooves 34 and that each face each other is disposed at a proximal end portion of the main body 28. The connection grooves 34 open inward and face each other.

Each of the connection grooves 34 includes a first groove 35 for fitting and a second groove 36 for separation. The second groove 36 has a groove width narrower than the first groove 35, and extends in the proximal end direction to a proximal end surface of the connection piece 38 from the groove 35 for fitting. The second groove 36 has a groove width W2 slightly larger than a width W1 of the support projection 32. The support projection 32 provided at the catheter hub 14 is inserted into each of the first grooves 35 provided at the pressing member 18. By this, the pressing member 18 is supported in a rotatable manner with respect to the catheter hub 14, using the support projection 32 as the axis of rotation.

Figure 7:
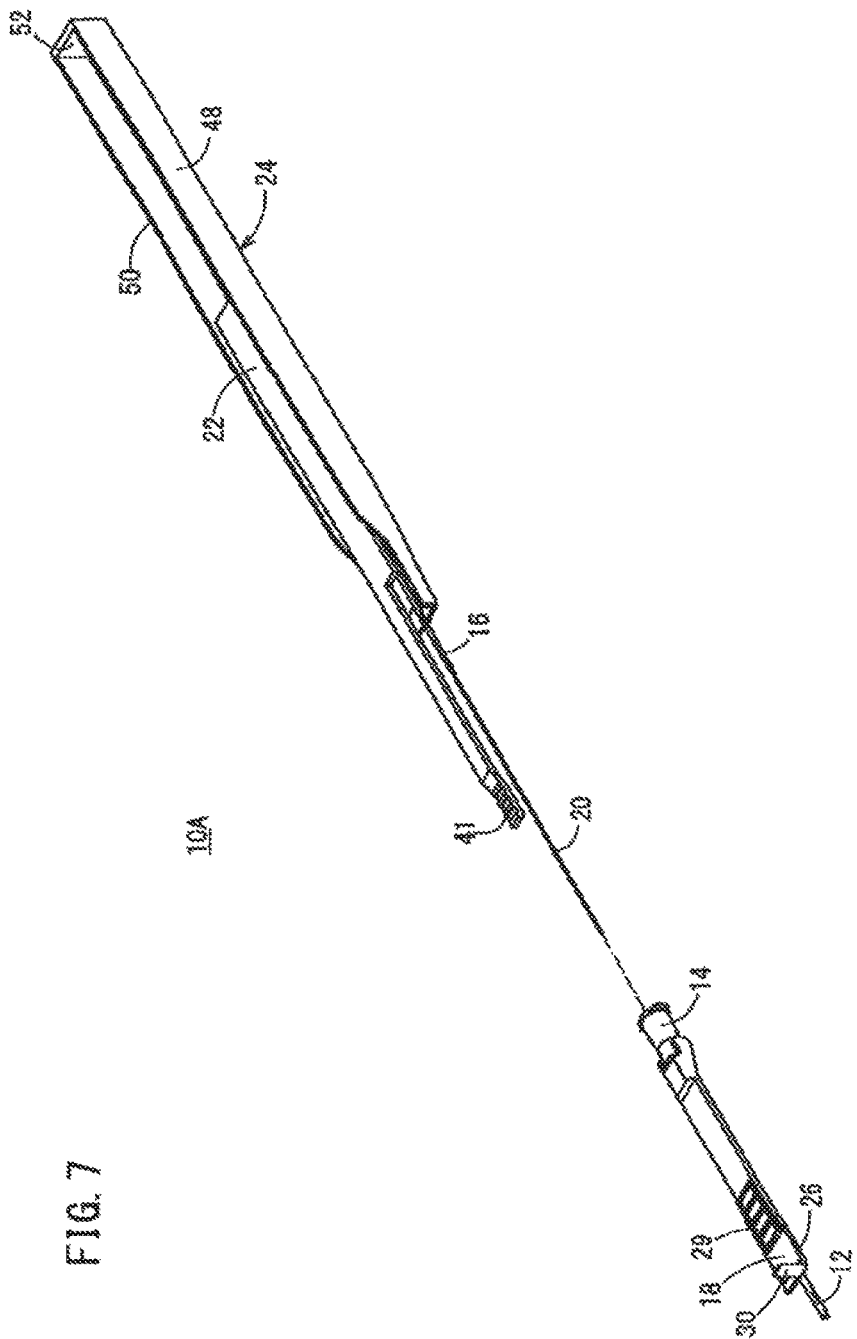
FIG. 7 is a third view illustrating the using method of the catheter assembly illustrated in FIG. 1.
Figure 8:
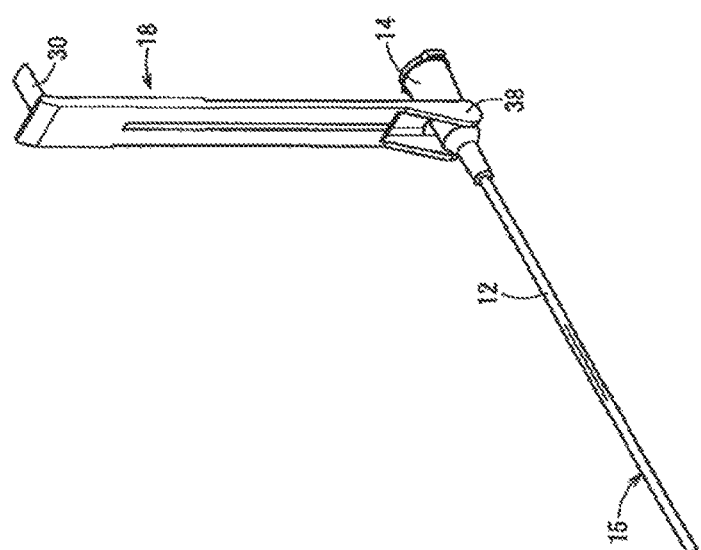
FIG. 8 is a fourth view illustrating the using method of the catheter assembly illustrated in FIG. 1.

The pressing member 18 is configured to be displaced to a first position located in the longitudinal (axial) direction of the catheter 12 (refer to FIG. 7) and a second position retracted from the catheter 12 (refer to FIG. 8). When the pressing member 18 is positioned at the first position, the pressing member 18 is positioned above the catheter 12, in axial overlapping relation to the catheter 12, and the distal end portion of the pressing member 18 (pressing portion 26) is positioned between the proximal end and the distal end of the catheter 12. Further, when the pressing member 18 is positioned at the first position, the support projection 32 is fitted into the first groove 35. Therefore, the pressing member 18 is prevented from separating from the catheter hub 14.

When the pressing member 18 is positioned at the second position, the pressing member 18 extends in a direction intersecting the longitudinal direction of the catheter 12 (substantially vertical direction with respect to the longitudinal direction of the catheter 12 in the illustrated present example). Further, when the pressing member 18 is positioned at the second position, the support projection 32 and the second groove 36 extend in the same direction. Therefore, the pressing member 18 can be separated from the catheter hub 14.

A constituent material from which the pressing member 18 is fabricated is not particularly limited, and for example, may be selected from the materials described above as examples of the constituent material of the catheter hub 14.

The guide wire 20 is a flexible linear member to guide the catheter 12 at the time of inserting the catheter 12 into the blood vessel in order to indwell the catheter 12 in the patient. The guide wire 20 is longer than the inner needle 16 and the catheter 12. The guide wire 20 has an outer diameter smaller than the inner diameter of the lumen 17 of the inner needle 16. When the catheter assembly 10A is in the assembled state, the distal end of the guide wire 20 is located on the more proximal end side than the needlepoint 16*a* of the inner needle 16 is, and is positioned in the vicinity of the needlepoint 16*a* in the illustrated present example. That is, in the assembled state of the assembly 10A, the distal end of the guide wire 20 is located proximally of the needlepoint 16*a* of the inner needle 16. The guide wire 20 is slidably inserted into the inner needle 16, and the distal end of the guide wire 20 can project from (distally beyond) the needlepoint 16*a*.

When the catheter assembly 10A is in the assembled state, the proximal end of the guide wire 20 is located on the more proximal end side than the proximal end of the catheter 12 (i.e., the proximal end of the guide wire 20 is positioned proximally of the proximal end of the catheter 12). The guide wire 20 has a length longer than respective lengths of the inner needle 16 and the catheter 12, and is, for example, about 40 to 1200 mm, and preferably, set to about 100 to 700 mm.

A constituent material of which the guide wire 20 is fabricated is not particularly limited, but for example, various kinds of metallic materials such as stainless steel and Ni—Ti-based alloy can be used. The guide wire 20 can have an entire length formed of a single material such as stainless steel or Ni—Ti-based alloy, but can be also formed of combination of different materials. An entire or a part of an outer peripheral surface (outer surface) of the guide wire 20 may be coated with a material having lubricity (PTFE, ETFE, etc., for example).

The wire operating member 22 is an operating portion to perform an inserting operation of the guide wire 20 into the blood vessel before performing an inserting operation of the catheter 12 into the blood vessel of the patient. In the present embodiment, the wire operating member 22 extends in the longitudinal direction of the inner needle 16 and the catheter 12, and is connected to the proximal end of the guide wire 20. More specifically, as illustrated in FIG. 2, the wire operating member 22 includes an elongated extending portion 40 extending in the longitudinal (axial) direction of the inner needle 16 and the catheter 12, and a wire holding potion 42 provided at the lower portion at the proximal end of the extending portion 40 and is configured to hold the proximal end of the guide wire 20.

The extending portion 40 is plate-shaped, and is slidable in the longitudinal direction on the pressing member 18. An uneven shape 41 is formed on the upper surface of the extending portion 40 at the distal end of the extending portion 40, and functions as a slip stopper at the time of performing an operation with touch of a finger.

A cut-out portion 44 extending in the longitudinal (axial) direction of the extending portion 40 is formed at the extending portion 40. The cut-out portion 44 reaches or extends to a most distal end portion of the extending portion 40. By providing such a cut-out portion 44, the finger hook projection 30 is prevented from interfering with movement of the wire operating member 22 at the time of moving the wire operating member 22 in the distal end direction with respect to the pressing member 18. Even in a state that the wire operating member 22 is moved in the distal end direction with respect to the pressing member 18 (refer to FIG. 5), it is possible to touch the finger hook projection 30 via the cut-out portion 44. Therefore, the pressing member 18 can be easily operated.

In the present example illustrated, the wire operating member 22 is longer than the pressing member 18, and the distal end portion of the wire operating member 22 is positioned above the portion of the pressing member 18 between the distal end and the proximal end of the pressing member 18 in the assembled state. The distal end portion of the wire operating member 22 thus axially overlaps a portion of the pressing member 18 located between the distal end and the proximal end of the pressing member 18 in the assembled state. The wire operating member 22 may have a length substantially the same as the pressing member 18, or a length shorter than the pressing member 18.

The gripping member 24 extends in the longitudinal (axial) direction of the inner needle 16 and the catheter 12, and possesses an elongated shape as a whole. As illustrated in FIG. 3, the gripping member 24 is connected to the inner needle 16 on a proximal end side of the inner needle 16, and also houses the pressing member 18 and the wire operating member 22 in a manner movable in the longitudinal (axial) direction in the assembled state. More specifically, as illustrated in FIG. 2, the gripping member 24 includes: a bottom plate 46; side walls 48, 50 extending upward from both right and left sides of the bottom plate 46; and a proximal end wall 52 upstanding at the proximal end of the bottom plate 46 and connecting the right and left side walls 48, 50. The upper side and the distal end side of the gripping member 24 are open. FIGS. 1 and 2 thus show that at least a portion of the gripping member 24 is a U-shaped portion in transverse cross-section, and the catheter hub 14 and the proximal end of the catheter 12 are positioned in the U-shaped portion of the gripping member 24 in the assembled state of the catheter assembly before use of the catheter assembly.

A guide groove 47 is formed at center in a lateral direction on the distal end side of the bottom plate 46, and extends in the longitudinal (axial) direction of the gripping member 24 up to a most distal end of the bottom plate 46. When the catheter 12 is moved in the distal end direction with respect to the gripping member 24, the catheter 12 is guided by the guide groove 47. Therefore, the catheter 12 can be stably moved without slipping off in the lateral direction.

The pressing member 18 and the wire operating member 22 are disposed inside the thus structured gripping member 24. The gripping member 24 functions as a guide member to control movement directions of the pressing member 18 and the wire operating member 22 when the pressing member 18 and the wire operating member 22 are moved in the distal end direction.

A needle holder 54 that holds the proximal end portion of the inner needle 16 is provided at the middle portion (intermediate location) in the longitudinal (axial) direction of the gripping member 24. The inner needle 16 and the gripping member 24 thus move together as a unit. The needle holder 54 is provided inside the gripping member 24 (between the right and left side walls 48, 50). As illustrated in FIG. 3, the needle holder 54 includes a holding hole 56, and the inner needle 16 is positioned in and fixed to the holding hole 56. The needle holder 54 includes an upper surface 54a formed as a slide surface to support the wire operating member 22 in a slidable manner. When the catheter assembly 10A is in the assembled state, the catheter member 15 and the pressing member 18 are housed inside the gripping member 24 on the more distal end side than the needle holder 54.

Thus, since the gripping member 24 holds the inner needle 16 at the needle holder 54, when the gripping member 24 is moved in the proximal end direction relative to the catheter 12, the inner needle 16 is also moved in the proximal end direction relative to the catheter 12 along with movement of the gripping member 24. In other words, the gripping member 24 also functions as the inner needle hub fixed to the proximal end of the inner needle 16. The catheter assembly 10A is configured so that the wire operating member 22 simultaneously axially overlaps a proximal portion of the pressing member 18, a proximal portion of the catheter 12, the catheter hub 14 and a proximal portion of the guide wire 20.

The catheter assembly 10A according to the present embodiment has the structure described above, and the operation and effects of the catheter assembly 10A will be described below.

As illustrated in FIG. 1, when the catheter assembly 10A is in the assembled state (initial state), the inner needle 16 is positioned in the catheter 12, and the needlepoint 16a projects from the distal end of the catheter 12 by a predetermined length, and the distal end of the guide wire 20 is located inside the inner needle 16. In the puncturing operation to puncture skin of the patient with the catheter assembly 10A in the assembled state, the user (doctor, nurse, etc.) grips the gripping member 24 with one hand (for example, right hand). Then, while pressing a distal end portion of the pressing member 18 with a forefinger of the mentioned one hand, the skin is punctured toward a blood vessel of a puncturing target in a manner pressing the distal end portion of the catheter assembly 10A (distal end portion of the catheter 12 inserted with the inner needle 16) against the patient. The needlepoint punctures the skin and then the blood vessel to provide access to the blood vessel.

In this case, according to the present embodiment, the inner needle 16 and the catheter 12 can be prevented from being deflected by pressing the middle portion between the proximal end and the distal end of the catheter 12 downward with the pressing member 18. In other words, in a state that the middle portion of the catheter 12 is pressed with the pressing member 18, the catheter 12 is supported by being sandwiched between the pressing member 18 (pressing portion 26 of the pressing member 18) and the gripping member 24 (bottom plate 46 of the gripping member 24). As a result, the inner needle 16 and the catheter 12 are prevented from being deflected. Therefore, the puncturing operation can be relatively easily performed even in the case where the inner needle 16 and the catheter 12 are relatively long.

Next, in a state the skin and blood vessel are punctured with the distal end portions of the inner needle 16 and the catheter 12, the wire operating member 22 is slightly advanced in the distal end direction by touching and slightly pushing the upper surface of the distal end portion of the wire operating member 22 with a forefinger of one hand while keeping or maintaining the position of the gripping member 24. By this, the guide wire 20 is made to project from the distal end of the inner needle 16 by several millimeters. Next, the guide wire 20 is moved in the distal end direction to a maximum extent by moving the wire operating member 22 in the distal end direction with the other hand (left hand, for example) (refer to FIG. 5). The guide wire 20 is inserted into the blood vessel along with movement of the guide wire 20 in the distal end direction.

Meanwhile, as illustrated by the virtual line in FIG. 5, a middle portion in the longitudinal (axial) direction of the wire operating member 22 may be configured to be curved or bent in a direction separating from the outer needle so that the middle portion of the wire operating member 22 moves away from outer needle. In this case, the wire operating member 22 can be bent by providing a hinge structure 58 formed of a thin portion (weakened portion) or by providing another hinge structure 58 including an axis and a bearing at the middle portion in the longitudinal direction of the wire operating member 22. Otherwise, the wire operating member 22 can be curved by forming the wire operating member 22 of a flexible member.

Since the wire operating member 22 is configured to be curved or bent, the middle portion of the wire operating member 22 is bent or curved even in the case where the distal end portion of the wire operating member 22 hits a part of the patient at the time of moving the wire operating member 22 in the distal end direction in order to insert the guide wire 20 into the blood vessel. Therefore, the wire operating member 22 can be prevented from interfering with the patient, and insertion of the guide wire 20 into the blood vessel can be relatively easily and surely performed.

Figure 6:
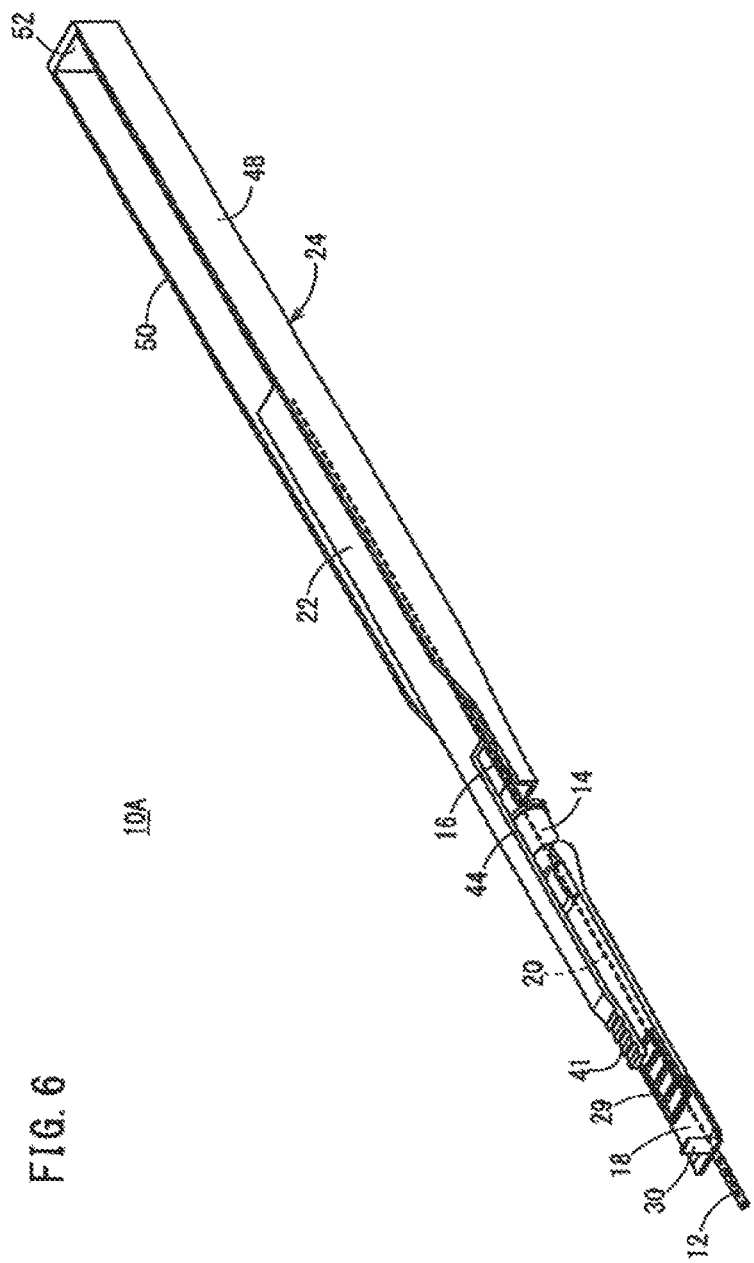
FIG. 6 is a second view illustrating the using method of the catheter assembly illustrated in FIG. 1.

When the distal end of the guide wire 20 is inserted up to a target position inside the blood vessel, the pressing member 18 is subsequently advanced by the forefinger of one hand by several millimeters, thereby advancing the catheter 12 by several millimeters. Next, the pressing member 18 is moved in the distal end direction by the other hand (refer to FIG. 6), thereby inserting the distal end of the catheter 12 up to the target position inside the blood vessel. At this point, the catheter 12 follows the guide wire 20 inserted into the blood vessel beforehand, more specifically, the catheter 12 is advanced inside the blood vessel, following the guide wire 20. Therefore, the distal end of the catheter 12 can be easily introduced up to the target position inside the blood vessel.

Figure 9:
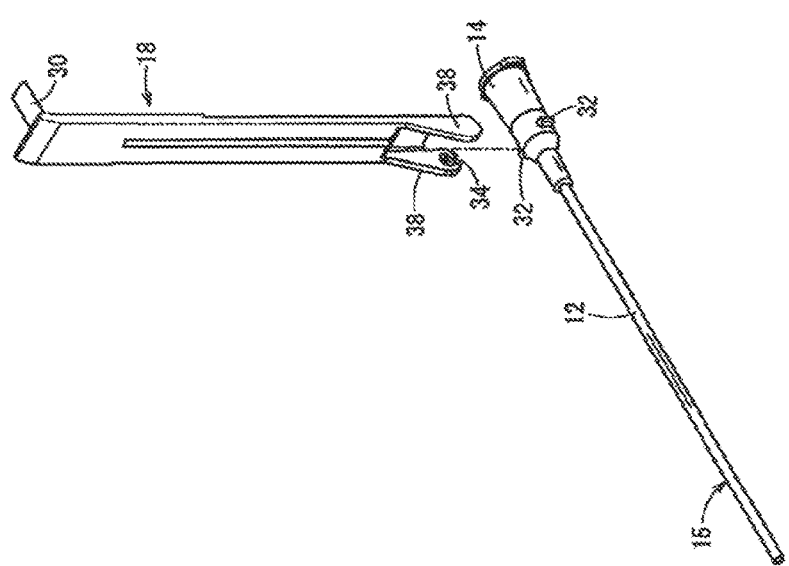
FIG. 9 is a fifth view illustrating the using method for the catheter assembly illustrated in FIG. 1.

Next, the gripping member 24 is gripped with one hand while pressing the pressing member 18 with the other hand, and the gripping member 24 is pulled in the proximal end direction. The inner needle 16 is thus removed from the catheter 12 as illustrated in FIG. 7. After removing the inner needle 16 from the catheter 12, the pressing member 18 may be detached from the catheter hub 14, if necessary. In this case, as illustrated in FIG. 8, the pressing member 18 is moved to the second position (standing upright in a substantially vertical posture with respect to the catheter hub 14 in the present embodiment). Next, as illustrated in FIG. 9, the pressing member 18 can be separated from the catheter hub 14 by pulling the pressing member 18 upward. Meanwhile, the pressing member 18 may also be kept attached to the catheter hub 14 after removing the inner needle 16 from the catheter 12.

Next, the connector of the infusion tube (not illustrated) is connected to a proximal end side of the catheter member 15 from which the inner needle 16 has been removed, and infusion material (chemical solution) is administered from the infusion tube to the patient.

As described above, according to the catheter assembly 10A of the present embodiment, when the skin is punctured with the respective distal end portions of the inner needle 16 and the catheter 12, the inner needle 16 and the catheter 12 can be prevented from being deflected by pressing the middle portion between the proximal end and the distal end of the catheter 12 downward with the pressing member 18. Therefore, the puncturing operation can be rather easily performed even in the case where the inner needle 16 and the catheter 12 are relatively long.

Further, after the puncturing operation, the guide wire 20 is inserted into the blood vessel before inserting the catheter 12 into the blood vessel. Therefore, the catheter 12 can be smoothly moved in the distal end direction along the guide wire 20. The distal end of the catheter 12 can thus be rather easily introduced to a target portion along the guide wire 20 even in a blood vessel that meanders and branches.

Further, since the catheter assembly 10A includes the wire operating member 22 extending along the pressing member 18, the moving operation of the guide wire 20 can be fairly easily performed.

In the case of the present embodiment, the wire operating member 22 is disposed in a manner superimposed on (axially overlapping) the pressing member 18. According to this structure, the catheter assembly 10A can be relatively easily gripped with excellent operability at the time of the puncturing operation and the like because the catheter assembly 10A can be formed thin.

In the case of the present embodiment, the finger hook projection 30 is provided at the distal end of the pressing member 18, and also the cut-out portion 44 is provided at the wire operating member 22. Therefore, the pressing member 18 can be operated by touching the pressing member 18 from above in a state that the distal end of the wire operating member 22 is advanced beyond the distal end of the pressing member 18 (state in FIG. 5). According to this structure, the wire operating member 22 is prevented from interfering and the pressing member 18 can be rather easily operated even in the state that the wire operating member 22 is moved in the distal end direction.

In the case of the present embodiment, the catheter assembly 10A includes the gripping member 24 that houses the pressing member 18 and the wire operating member 22 in a manner movable in the longitudinal (axial) direction. According to this structure, the gripping member 24 can be gripped with a hand in respective operations: at the time of puncturing a skin with the respective distal ends of the inner needle 16 and the catheter 12; at the time of moving the catheter 12 in the distal end direction when moving the guide wire 20 in the distal end direction; and at the time of pulling out the inner needle 16 from the catheter 12. Therefore, the respective operations can be easily performed.

Figure 10:
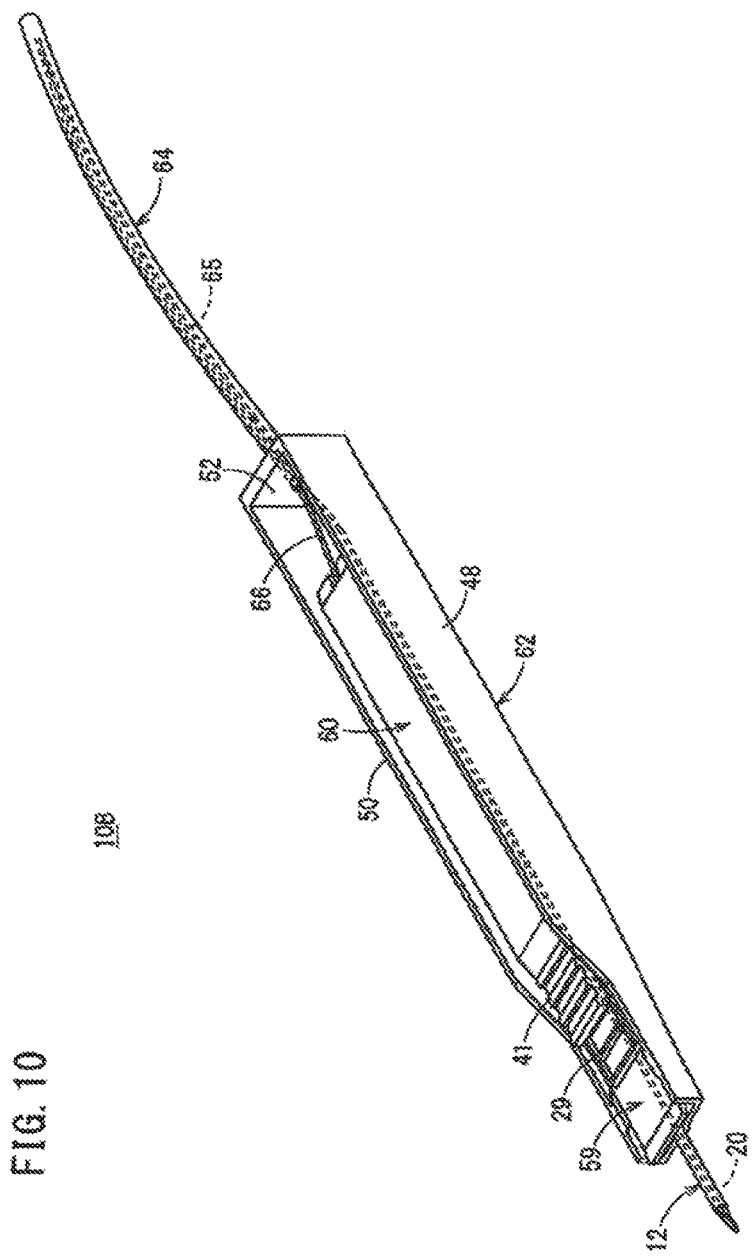
FIG. 10 is a perspective view illustrating a catheter assembly according to a second embodiment disclosed here.
Figure 11:
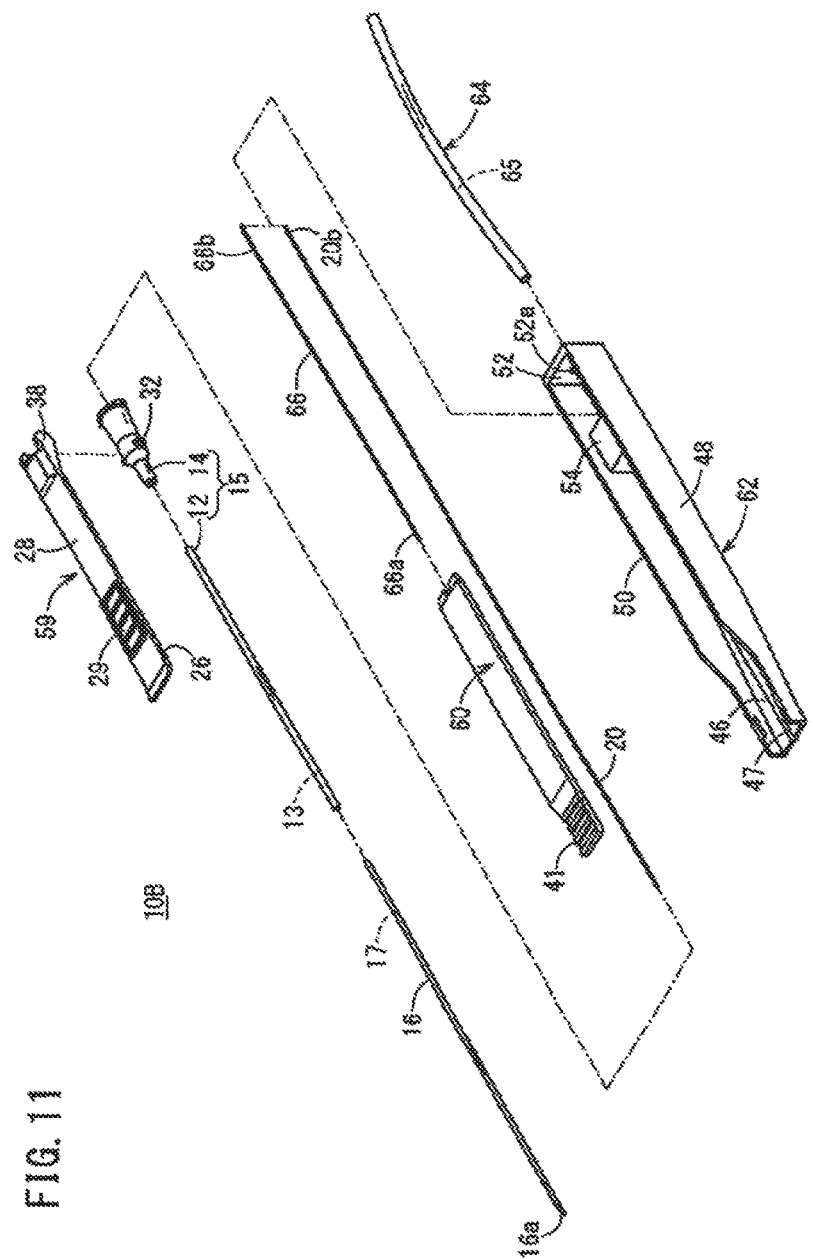
FIG. 11 is an exploded perspective view illustrating the catheter assembly illustrated in FIG. 10.
Figure 12:
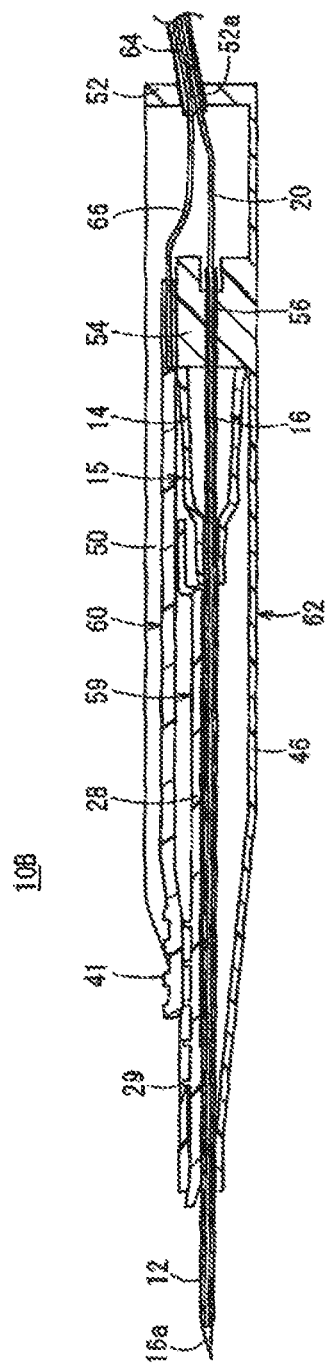
FIG. 12 is a partly-omitted vertical cross-sectional view illustrating the catheter assembly illustrated in FIG. 10.

FIGS. 10-12 illustrate a catheter assembly 10B according to a second embodiment. Components in the catheter assembly 10B according to the second embodiment that provide functions and effects the same as or similar to components in the catheter assembly 10A according to the first embodiment are denoted by the same reference numerals, and a detailed description of such aspects of the catheter assembly are not repeated.

The catheter assembly 10B includes a catheter member 15, an inner needle 16, and a guide wire 20 the same as the catheter assembly 10A according to the first embodiment. The catheter assembly 10B differs from the catheter assembly 10A according to the first embodiment with respect to the structures constituting a pressing member 59, a wire operating member 60, and a gripping member 62. Further, the catheter assembly 10B differs from the catheter assembly 10A according to the first embodiment in including an operating wire 66 and a wire housing portion 64. A description of these different aspects of the catheter assembly 10B is set forth next.

The pressing member 59 differs from the pressing member 18 in the first embodiment in that the pressing member 59 does not include a finger hook projection 30.

The wire operating member 60 extends in a longitudinal (axial) direction of the inner needle 16 and a catheter 12, and has a common point with the wire operating member 22 of the first embodiment in that the wire operating member 60 is displaceable in the longitudinal (axial) direction relative to the inner needle 16 and the catheter 12. The wire operating member 60 is shorter than the wire operating member 22 in the first embodiment. The wire operating member 60 is disposed in a manner superimposed on or axially overlapping the pressing member 59, and slidable in the longitudinal direction on the pressing member 59. A distal end portion 66a of the operating wire 66 is connected and fixed to a proximal end portion of the wire operating member 60.

The operating wire 66 has a proximal end side (proximal end portion 66b) connected to the guide wire 20, and is a linear member to move the guide wire 20. The operating wire 66 may be shorter than the guide wire 20. The portion of the guide wire 20 and the operating wire 66 that are distal of the connected portions (i.e., the connected portions 20b, 66b at which the guide wire 20 and the operating wire 66 are connected) are separated from each other and are not joined to each other. A constituent material from which the operating wire 66 is fabricated is not particularly limited as far as the above function can be achieved, but the constituent material may be same as the guide wire 20, for example. Preferably, the operating wire 66 is a flexible linear member.

The gripping member 62 houses the pressing member 59 and the wire operating member 60 in a manner movable in the longitudinal direction. The gripping member 62 is shorter than a gripping member 24 in the first embodiment. More specifically, the length on the proximal end side of the needle holder 54 of the gripping member 62 is shorter than that of the gripping member 24 of the first embodiment. A through-hole 52a is provided at a proximal end wall 52 of the gripping member 62. A distal end portion of the wire housing portion 64 is fixed at the through-hole 52a.

The wire housing portion 64 is a flexible tubular member having a relatively small inner diameter. The wire housing portion 64 is disposed more proximally than the inner needle 16, and is configured to house the guide wire 20 and the operating wire 66 in a state that respective proximal end portions of the guide wire 20 and the operating wire 66 are axially overlapping (in a bundled state). In other words, respective portions out of the guide wire 20 and the operating wire 66, which are inserted into (housed inside) the wire housing portion 64, are set in the bundled (superimposed) state inside a lumen 65 of the wire housing portion 64. When the catheter assembly 10B is in an assembled state (assembled state), the respective proximal end portions 20b, 66b of the guide wire 20 and the operating wire 66 are housed in the wire housing portion 64.

The catheter assembly 10B according to the present embodiment has the structure described above, and the operations and effects of the catheter assembly 10B are described below.

As illustrated in FIG. 10, when the catheter assembly 10B is in the assembled state, the inner needle 16 is inserted into the catheter 12, and a needlepoint 16a projects from a distal end of the catheter 12 by a predetermined length, and a distal end of the guide wire 20 is located in the inner needle 16. In a puncturing operation to puncture skin of a patient with the catheter assembly 10B in such an assembled state, a user (doctor, nurse, etc.) grips the gripping member 62 with one hand. Then, while pressing a distal end portion of the pressing member 59 with a forefinger of the mentioned one hand, the skin is punctured toward a blood vessel of a puncturing target in a manner pressing the distal end portion of the catheter assembly 10B (distal end portion of the catheter 12 inserted with the inner needle 16) against the patient. The needlepoint 16A punctures the skin and then the blood vessel to provide access to the blood vessel.

In this case, the middle portion between a proximal end and a distal end of the catheter 12 is sandwiched and supported between the pressing member 59 and the gripping member 62 by pressing the middle portion of the catheter 12 downward with the pressing member 59. As a result, the inner needle 16 and the catheter 12 can be prevented from being deflected. Therefore, the puncturing operation can be easily performed even in the case where the inner needle 16 and the catheter 12 are relatively long.

Figure 13:
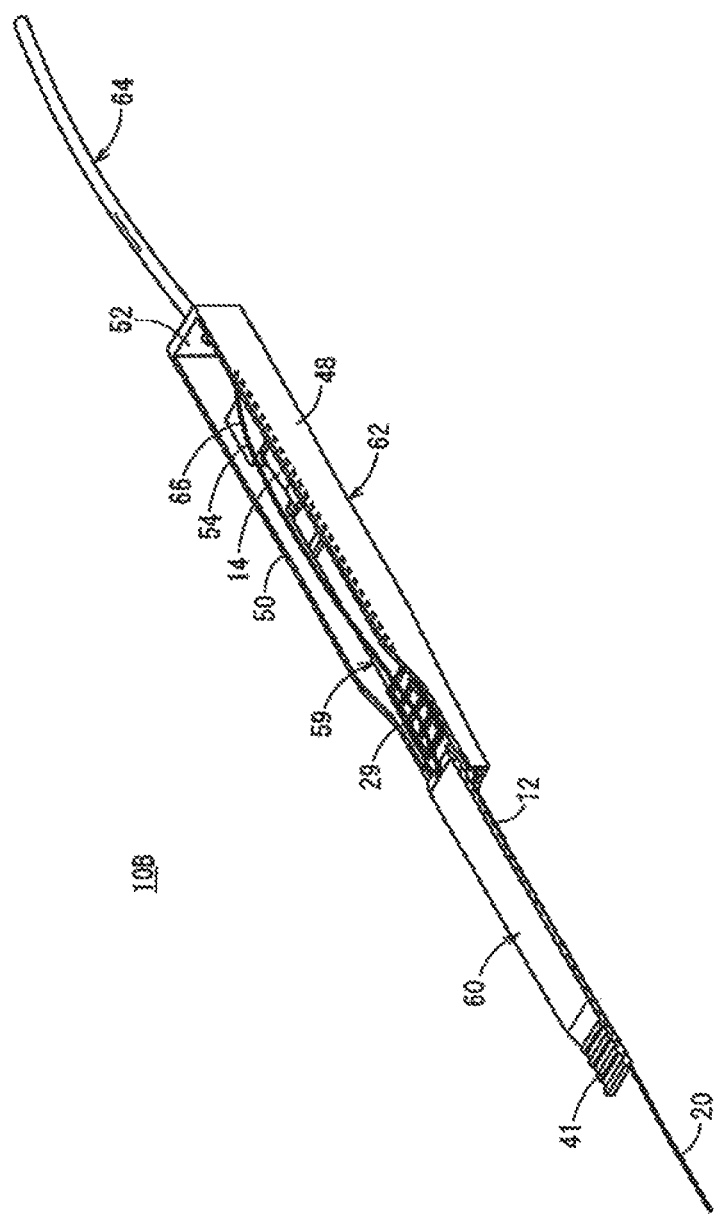
FIG. 13 is a first view illustrating the using method of the catheter assembly illustrated in FIG. 10.

Next, in a state that the skin and blood vessel are punctured with the distal end portions of the inner needle 16 and the catheter 12, the wire operating member 60 is slightly advanced in the distal end direction by touching and slightly pushing the upper surface of a distal end portion of the wire operating member 60 with a forefinger of one hand while keeping or maintaining the position of the gripping member 62. The guide wire 20 is thus axially moved to project from the distal end of the inner needle 16 by several millimeters. Next, the guide wire 20 is moved in the distal end direction to a maximum extent by moving the wire operating member 60 in the distal end direction with the other hand (refer to FIG. 13). The guide wire 20 is inserted into the blood vessel along with movement of the guide wire 20 in the distal end direction.

In this case, since a proximal end portion of the guide wire 20 is housed in the wire housing portion 64, the guide wire 20 is prevented from being deflected at the time of advancing the guide wire 20. In other words, a portion of the guide wire 20 on the proximal side of the proximal end of the inner needle 16, which is not supported by the wire housing portion 64, is only a relatively short portion from the proximal end of the inner needle 16 to the wire housing portion 64. Further, the guide wire 20 is flexible, but also has a certain level of rigidity to stand against bending deformation. Therefore, when force is applied in the distal end direction from the proximal end portion 20b of the guide wire 20 via the operating wire 66, the portion of the guide wire 20 between the proximal end of the inner needle 16 and the wire housing portion 64 is prevented from being deflected by the own rigidity of the guide wire 20.

Further, according to the present embodiment, the wire housing portion 64 does not become an obstacle because the flexible wire housing portion 64 can be curved and prevented from interfering with the patient even in the case where the wire housing portion 64 hits a part of the patient. In other words, the entire length of the catheter assembly 10B tends to be elongated by including the guide wire 20, compared to a structure not including the guide wire 20. However, the wire housing portion 64, and the guide wire 20 and the operating wire 66 housed inside the wire housing portion 64, are all flexible and can be rather easily deformed when an external force is applied. Therefore, these components do not become obstacles at the time of using the catheter assembly 10B.

Figure 14:
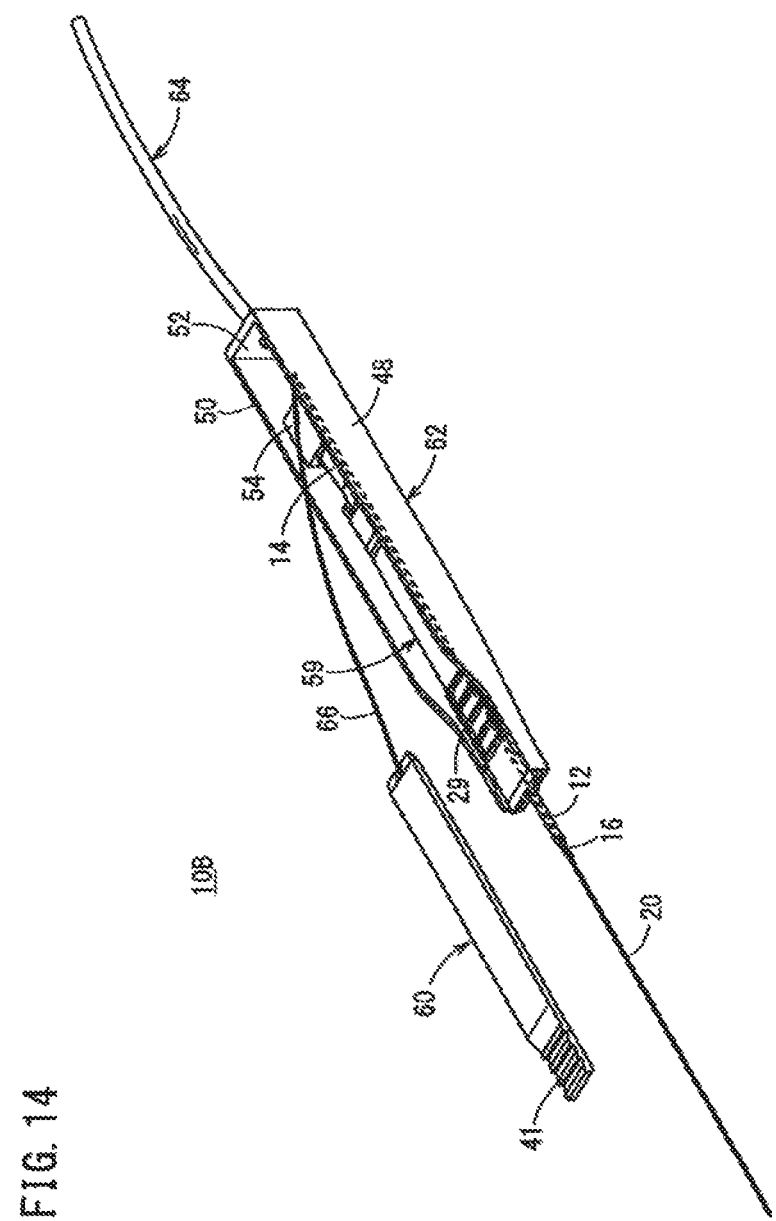
FIG. 14 is a second view illustrating the using method of the catheter assembly illustrated in FIG. 10.

When the distal end of the guide wire 20 is inserted up to the target position inside the blood vessel, the wire operating member 60 is subsequently moved to a position deviated in a lateral direction from above the pressing member 59 by using the other hand as illustrated in FIG. 14. In the case of the present embodiment, the wire operating member 60 and the guide wire 20 are connected by the flexible operating wire 66, and further the wire operating member 60 can be separated from the gripping member 62. Therefore, the wire operating member 60 can be easily moved to a position deviated from above the pressing member 59. A subsequent operation for the pressing member 59 can thus be easily performed.

Figure 15:
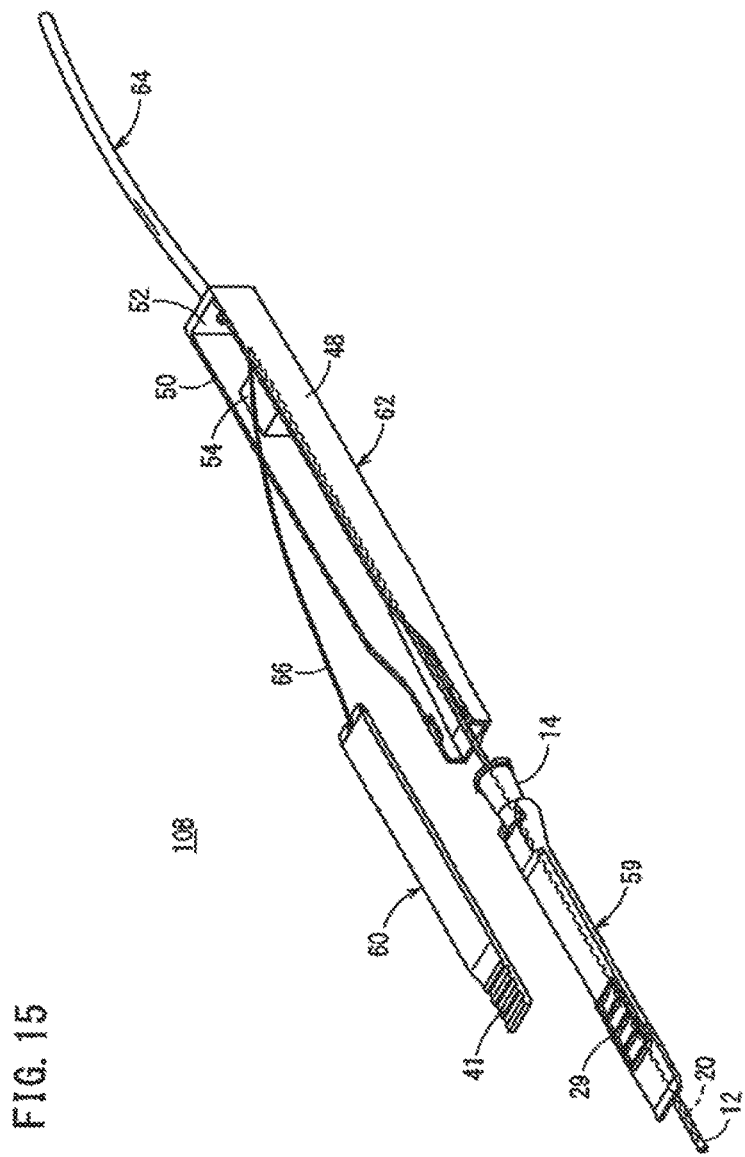
FIG. 15 is a third view illustrating the using method of the catheter assembly illustrated in FIG. 10.

Next, the pressing member 59 is advanced by several millimeters in the distal end direction by the forefinger of one hand, thereby advancing the catheter 12 by several millimeters. Next, the pressing member 59 is moved in the distal end direction by the other hand as illustrated in FIG. 15. The distal end of the catheter 12 is thus inserted up to the target position inside the blood vessel. At this point, the catheter 12 follows the guide wire 20 inserted into the blood vessel beforehand, more specifically, the catheter 12 is advanced inside the blood vessel, following the guide wire 20. Therefore, the distal end of the catheter 12 can be easily introduced up to the target position inside the blood vessel.

Figure 16:
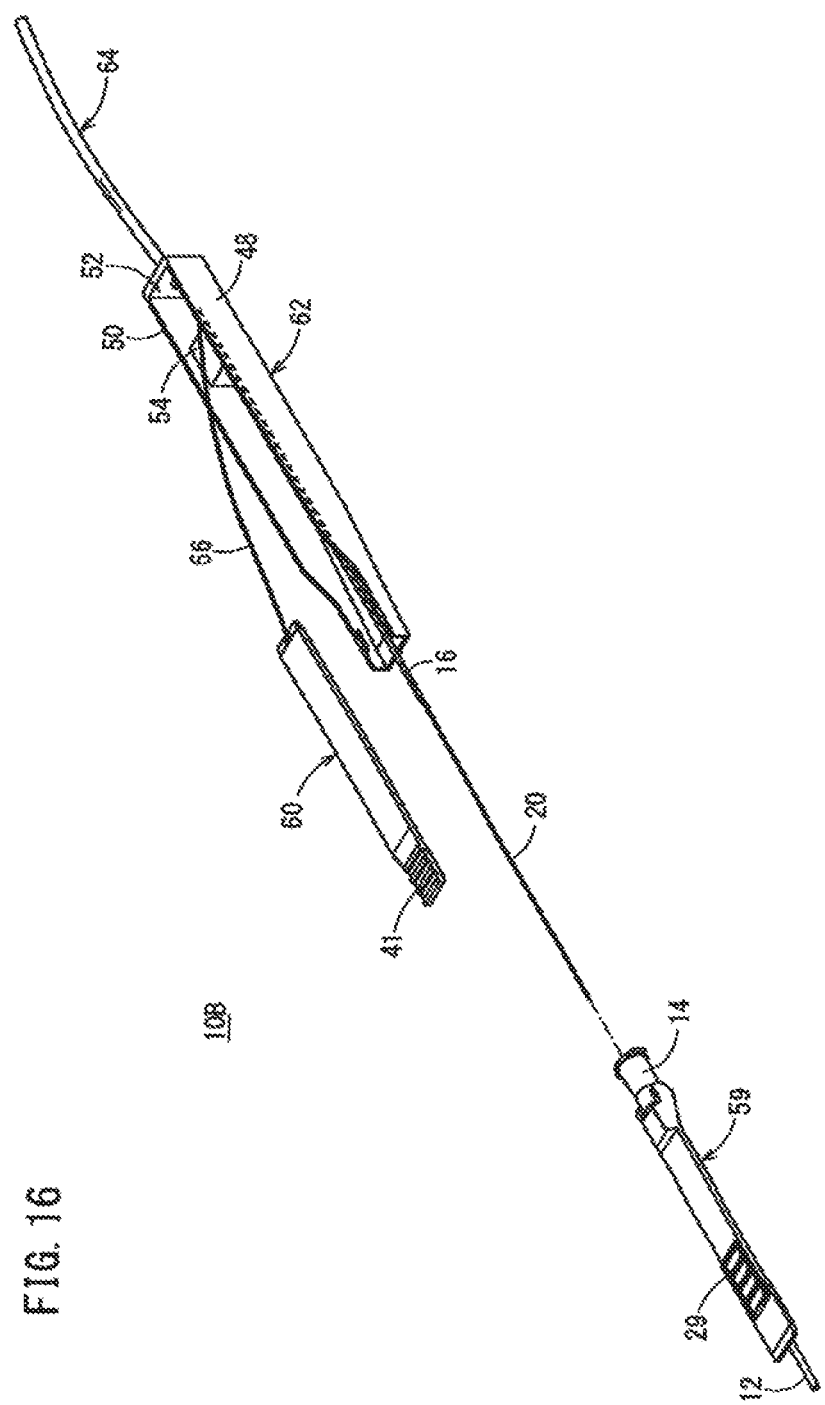
FIG. 16 is a fourth view illustrating the using method of the catheter assembly illustrated in FIG. 10.
Figure 17:
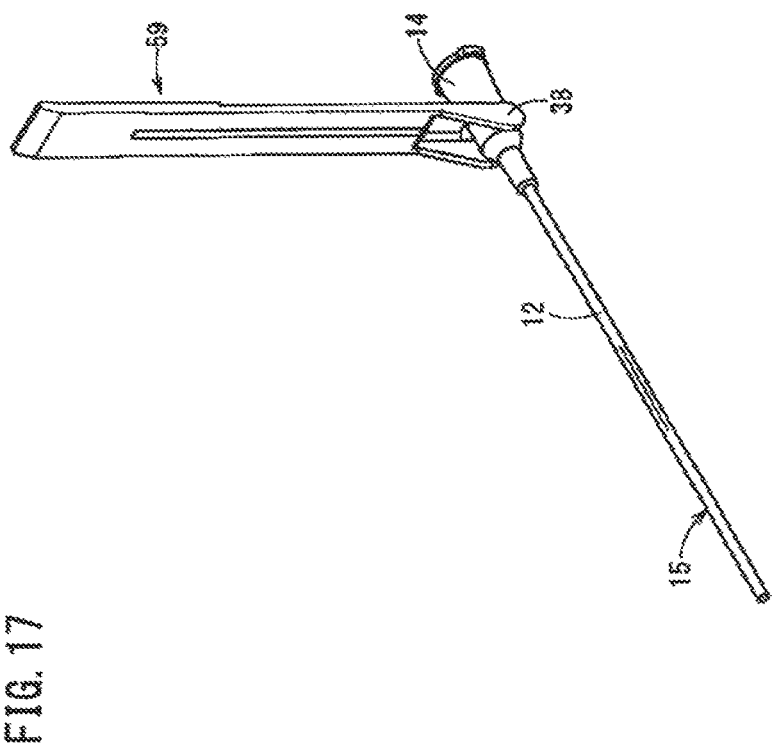
FIG. 17 is a fifth view illustrating the using method of the catheter assembly illustrated in FIG. 10.
Figure 18:
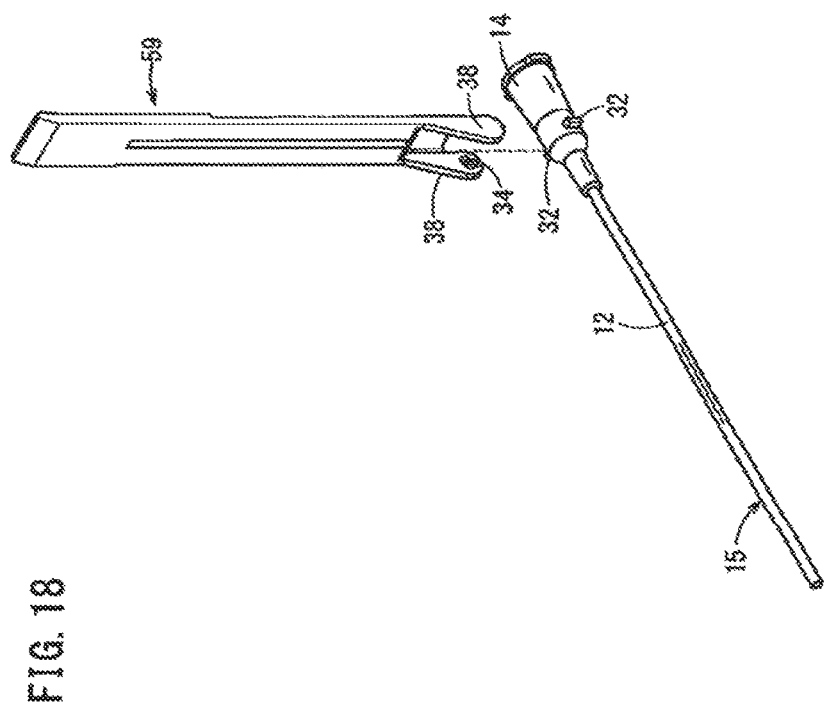
FIG. 18 is a sixth view illustrating the using method of the catheter assembly illustrated in FIG. 10.

Next, the gripping member 62 is gripped with one hand while pressing the pressing member 59 with the other hand, and the gripping member 62 is pulled in the proximal end direction. This causes the inner needle 16 to be removed from the catheter 12 as illustrated in FIG. 16. After removing the inner needle 16 from the catheter 12, the pressing member 59 may be detached from the catheter hub 14, if necessary. In this case, as illustrated in FIG. 17, the pressing member 59 is moved to a second position (standing upright in a substantially vertical posture with respect to the catheter hub 14 in the present embodiment). Next, as illustrated in FIG. 18, the pressing member 59 can be separated from the catheter hub 14 by pulling the pressing member 59 upward. It is also possible to keep the pressing member 59 attached to the catheter hub 14 after removing the inner needle 16 from the catheter 12.

Next, the connector of the infusion tube (not illustrated) is connected to a proximal end side of the catheter member 15 from which the inner needle 16 has been removed, and infusion material (chemical solution) is administered from the infusion tube to the patient.

As described above, when the skin is punctured with the respective distal end portions of the inner needle 16 and the catheter 12, the inner needle 16 and the catheter 12 can be prevented from being deflected by pressing the middle portion between the proximal end and the distal end of the catheter 12 downward with the pressing member 59. Therefore, the puncturing operation can be relatively easily performed even in the case where the inner needle 16 and the catheter 12 are relatively long.

Further, after the puncturing operation, the guide wire 20 is inserted into the blood vessel before inserting the catheter 12 into the blood vessel. Therefore, the catheter 12 can be moved in the distal end direction along the guide wire 20. As a result, the distal end of the catheter 12 can be rather easily introduced to a target portion along the guide wire 20 even in the blood vessel having meandering and branching.

Further, since the portion on the proximal end side of the guide wire 20 is housed in the wire housing portion 64, the guide wire 20 on the more proximal end side than the inner needle 16 is prevented from being deflected at the time of advancing the guide wire 20.

Further, the flexible wire housing portion 64 can be curved and prevented from interfering with the patient even in the case where the wire housing portion 64 hits a part of the patient. Therefore, the wire housing portion 64 does not become an obstacle.

Further, in the case of the present embodiment, the wire operating member 60 can be moved to a position deviated in the lateral direction from above the pressing member 59 in a state that the wire operating member 60 is moved from an initial position in the distal end direction (refer to FIG. 14). According to this structure, the wire operating member 60 is separated from the pressing member 59 after moving the wire operating member 60 in the distal end direction in order to insert the guide wire 20 into the blood vessel. As a result, the wire operating member 60 does not become an obstacle at the time of easily operating the pressing member 59.

It is to be understood that the respective components in the second embodiment that are the same as those in the first embodiment can achieve the functions and effects the same as or similar to the functions and effects brought by the respective components of the first embodiments.

The detailed description above describes embodiments of a catheter assembly representing examples of the inventive catheter assembly disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter assembly comprising:
a catheter possessing a distal end, a proximal end and a proximal end portion;
a catheter hub fixed to the proximal end portion of the catheter, the catheter hub possessing a proximal-most end;
a hollow inner needle positioned inside the catheter and removable from inside the catheter, the needle possessing a distal end, and the needle including a needlepoint at the distal end of the needle;
a gripping member connected to a proximal portion of the inner needle and extending in a longitudinal direction;
a catheter operating member connected to the catheter hub and movable in the longitudinal direction relative to the inner needle, the catheter operating member including an operating portion;

the operating portion of the catheter operating member possessing a part to which a force is applied by a user to move the catheter relative to the inner needle from a position in which a distal-most end of the catheter is positioned proximal to the needlepoint to a position in which the distal-most end of the catheter is positioned distal to the needlepoint;

a guide wire slidably positioned in the inner needle and possessing a distal end, the guide wire possessing a length longer than the inner needle and longer than the catheter, the guide wire being configured so that the distal end of the guide wire projects distally beyond the needlepoint during use of the catheter assembly;

a wire operating member connected to the guide wire so that movement of the wire operating member results in movement of the guide wire, the wire operating member being movable in the longitudinal direction relative to the inner needle and the catheter, the wire operating member including an operating portion;

the wire operating member that moves together with the guide wire possessing a distal-most end that axially overlaps a part of the catheter operating member when the distal-most end of the catheter is positioned proximal of the needlepoint before use of the catheter assembly;

the operating portion of the wire operating member possessing a part to which a force is applied by the user to move the guide wire relative to the catheter and the inner needle; and the catheter operating member being configured to press a portion of the catheter between the proximal end of the catheter and the distal end of the catheter when the user presses on the catheter operating member while puncturing a living body with the needlepoint.

2. The catheter assembly according to claim 1, wherein the catheter operating member includes a main body section that is removably connected to the catheter hub.

3. The catheter assembly according to claim 2, wherein the main body section of the catheter operating member possesses an elongated configuration.

4. The catheter assembly according to claim 2, wherein the part of the operating portion of the catheter operating member to which the force is applied includes a projection grippable by a hand of the user to advance the catheter, the projection being upstanding relative to the main body section so that the projection projects away from the main body section.

5. The catheter assembly according to claim 1, wherein the part of the operating portion of the catheter operating member to which the force is applied includes a projection that projects from a main body section mounted on the catheter hub.

6. The catheter assembly according to claim 1, wherein the wire operating member axially overlaps the catheter operating member in an assembled state of the catheter assembly before use of the catheter assembly.

7. The catheter assembly according to claim 6, wherein the catheter operating member includes a main body section connected to the catheter hub, the operating portion of the wire operating member overlying the main body section of the catheter operating member.

8. The catheter assembly according to claim 7, wherein the wire operating member is slidable in the longitudinal direction relative to the main body section of the catheter operating member.

9. The catheter assembly according to claim 1, wherein the wire operating member simultaneously axially overlaps at least a portion of the catheter operating member, at least a portion of the catheter hub, at least a portion of the inner needle and at least a portion of the guide wire in an assembled state of the catheter assembly before use of the catheter assembly.

10. The catheter assembly according to claim 1, wherein at least a portion of the gripping member is a U-shaped portion possessing a U-shape in transverse cross-section, the catheter hub and the proximal end of the catheter being positioned in the U-shaped portion of the gripping member in an assembled state of the catheter assembly before use of the catheter assembly.

11. The catheter assembly according to claim 10, wherein the U-shaped portion of the gripping member includes two opposed wall sections; the catheter hub and the proximal end of the catheter being positioned between the two opposed wall sections.

12. The catheter assembly according to claim 1, wherein the gripping member possesses a distal end portion provided with a guide groove, the catheter being positioned in the guide groove.

13. The catheter assembly according to claim 1, wherein the catheter hub possesses an outer surface, and the catheter operating member includes a main body section that is removably connected to the outer surface of the catheter hub.

14. The catheter assembly according to claim 13, wherein the main body section includes two connection pieces that are removably connected to the outer surface of the catheter hub.

15. The catheter assembly according to claim 14, wherein the catheter hub is positioned between the two connection pieces in an assembled state of the catheter assembly before use of the catheter assembly.

16. The catheter assembly according to claim 1, wherein the distal end portion of the operating portion of the wire operating member to which the force is applied by the user is positioned distal of the proximal-most end of the catheter hub in an assembled state of the catheter assembly before use of the catheter assembly.

17. A catheter assembly comprising:
a catheter possessing a distal end, a proximal end and a proximal end portion;
a catheter hub fixed to the proximal end portion of the catheter, the catheter hub possessing a proximal-most end;
a hollow inner needle positioned inside the catheter and removable from inside the catheter, the needle possessing a distal end, and the needle including a needlepoint at the distal end of the needle;
a gripping member connected to a proximal portion of the inner needle and extending in a longitudinal direction;
a catheter operating member connected to the catheter hub and movable in the longitudinal direction relative to the inner needle, the catheter operating member including an operating portion;
the operating portion of the catheter operating member possessing a part to which a force is applied by a user to move the catheter relative to the inner needle from a position in which a distal-most end of the catheter is positioned proximal to the needlepoint to a position in which the distal-most end of the catheter is positioned distal to the needlepoint;
a guide wire slidably positioned in the inner needle and possessing a distal end, the guide wire possessing a length longer than the inner needle and longer than the catheter, the guide wire being configured so that the distal end of the guide wire projects distally beyond the needlepoint during use of the catheter assembly;

a wire operating member connected to the guide wire so that movement of the wire operating member results in movement of the guide wire, the wire operating member being movable in the longitudinal direction relative to the inner needle and the catheter, the wire operating member including an operating portion;

the wire operating member that moves together with the guide wire possessing a distal-most end portion at which are located a plurality of upstanding projections to inhibit finger slippage during movement of the wire operating member in the longitudinal direction, the plurality of upstanding projections including three distal-most upstanding projections, the three distal-most projections including a first upstanding projection, a second upstanding projection and a third upstanding projection, the first upstanding projection being distal of the second and third upstanding projections, the second upstanding projection being positioned between the first upstanding projection and the third upstanding projection in the longitudinal direction, the first and second upstanding projections being spaced apart from one another in the longitudinal direction, the second and third projections being spaced apart from one another in the longitudinal direction, the second and third upstanding projections axially overlapping a part of the catheter operating member when the distal-most end of the catheter is positioned proximal of the needlepoint before use of the catheter assembly;

the operating portion of the wire operating member possessing a part to which a force is applied by the user to move the guide wire relative to the catheter and the inner needle; and the catheter operating member being configured to press a portion of the catheter between the proximal end of the catheter and the distal end of the catheter when the user presses on the catheter operating member while puncturing a living body with the needlepoint.

18. The catheter assembly according to claim 17, wherein the wire operating member axially overlaps the catheter operating member in the assembled state of the catheter assembly before use of the catheter assembly.

19. A catheter assembly comprising:

a catheter possessing a distal end, a proximal end and a proximal end portion;

a catheter hub fixed to the proximal end portion of the catheter, the catheter hub possessing a proximal-most end;

a hollow inner needle positioned inside the catheter and removable from inside the catheter, the needle possessing a distal end, and the needle including a needlepoint at the distal end of the needle;

a gripping member connected to a proximal portion of the inner needle and extending in a longitudinal direction;

a catheter operating member connected to the catheter hub and movable in the longitudinal direction relative to the inner needle, the catheter operating member including an operating portion;

the operating portion of the catheter operating member possessing a part to which a force is applied by a user to move the catheter relative to the inner needle from a position in which a distal-most end of the catheter is positioned proximal to the needlepoint to a position in which the distal-most end of the catheter is positioned distal to the needlepoint;

a guide wire slidably positioned in the inner needle and possessing a distal end, the guide wire possessing a length longer than the inner needle and longer than the catheter, the guide wire being configured so that the distal end of the guide wire projects distally beyond the needlepoint during use of the catheter assembly;

a wire operating member connected to the guide wire so that movement of the wire operating member results in movement of the guide wire, the wire operating member being movable in the longitudinal direction relative to the inner needle and the catheter, the wire operating member including an operating portion;

the wire operating member that moves together with the guide wire possessing a distal-most end portion at which are located a plurality of upstanding projections to inhibit finger slippage during movement of the wire operating member in the longitudinal direction, the plurality of upstanding projections including two distal-most upstanding projections, the two distal-most projections including a first upstanding projection and a second upstanding projection that are spaced apart from one another in the longitudinal direction so that a space exists between the first and second upstanding projections, at least a portion of the space axially overlapping a part of the catheter operating member when the distal-most end of the catheter is positioned proximal of the needlepoint before use of the catheter assembly;

the operating portion of the wire operating member possessing a part to which a force is applied by the user to move the guide wire relative to the catheter and the inner needle; and the catheter operating member being configured to press a portion of the catheter between the proximal end of the catheter and the distal end of the catheter when the user presses on the catheter operating member while puncturing a living body with the needlepoint.

20. The catheter assembly according to claim 19, wherein the wire operating member simultaneously axially overlaps at least a portion of the catheter operating member, at least a portion of the catheter hub, at least a portion of the inner needle and at least a portion of the guide wire in the assembled state of the catheter assembly before use of the catheter assembly.

* * * * *